| United States Patent [19] | [11] 4,011,221 |
| --- | --- |
| Sakakibara et al. | [45] Mar. 8, 1977 |

[54] S-INOSYLCYSTEINE AND A PROCESS FOR PRODUCING THE SAME

[75] Inventors: Eiichi Sakakibara, Takarazuka; Iwao Hashimoto, Osaka; Mitsuru Hirohashi, Katano, all of Japan

[73] Assignee: Funai Pharmaceutical Industries, Ltd., Japan

[22] Filed: Aug. 21, 1975

[21] Appl. No.: 606,478

[30] Foreign Application Priority Data

Aug. 22, 1974   Japan ............................. 49-95527

[52] U.S. Cl. ............................... 260/252; 536/24; 424/253
[51] Int. Cl.² ...................................... C07D 473/30
[58] Field of Search ................................. 260/252

[56] References Cited

UNITED STATES PATENTS

| 1,978,881 | 10/1934 | Lautenschlager et al. ..... 260/252 X |
| 3,170,917 | 2/1965 | Lauter et al. ................. 260/252 X |

FOREIGN PATENTS OR APPLICATIONS 1,178,329   1/1970   United Kingdom ............... 260/252

Primary Examiner—Donald G. Daus
Assistant Examiner—D. B. Springer
Attorney, Agent, or Firm—Hill, Gross, Simpson, Van Santen, Steadman, Chiara & Simpson

[57] ABSTRACT

S-Inosylcysteine, possessing a cell-proliferating activity and useful in the treatment of tissue lesions and ulcers, is produced by reacting a 2', 3'-O-protected-inosine derivative with an alkali metal salt of cysteine to produce S-(2', 3'-O-protected-inosyl) cysteine, and then removing the protecting group.

1 Claim, No Drawings

S-INOSYLCYSTEINE AND A PROCESS FOR PRODUCING THE SAME

BACKGROUND OF THE INVENTION

1. Field of the Invention

This invention is in the field of inosine derivatives and specifically is directed to S-inosylcysteine.

2. Description of the Prior Art

Inosine is a material which occurs naturally in meat, meat extracts, and in sugar beets. Generally, no pharmaceutical use has ever been made of this material. Cysteine is an amino acid which has been prepared from proteins by hydrolysis in the presence of carbon dioxide or by other means. The only medical use reported for this material has been in the promotion of wound healing.

SUMMARY OF THE INVENTION

The present invention is directed to a novel S-inosylcysteine and to a method for its preparation. The method of the invention involves reacting a 2',3'-O-protected inosine derivative with alkali metal salts of cysteine to produce S-(2', 3'-O-protected-inosyl) cysteine and then removing the protecting group.

DESCRIPTION OF THE PREFERRED EMBODIMENTS

The inventors have now found that S-inosylcysteine [5'-S-(2-amino-2-carboxyethyl)-5'-thioinosine] represented by structural formula (III) exhibits a remarkable cell-proliferating activity and is useful in the treatment of tissue lesion, ulcers and the like.

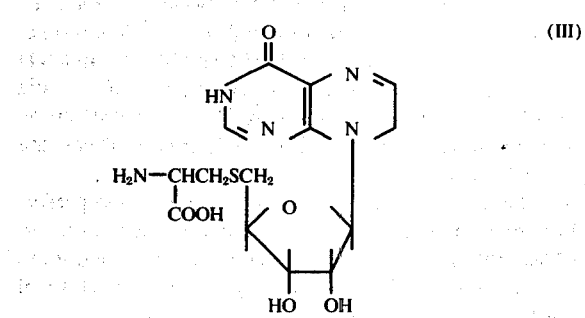

According to the present invention, S-inosylcysteine of the formula (III) is prepared by reacting 2', 3'-O-protected-inosine derivatives of the formula (I) with alkali metal salts of the formula (IV) to produce S-(2', 3'-O-protected-inosyl) cysteine of the formula (II), and then removing the protecting group, according to the following series of equations:

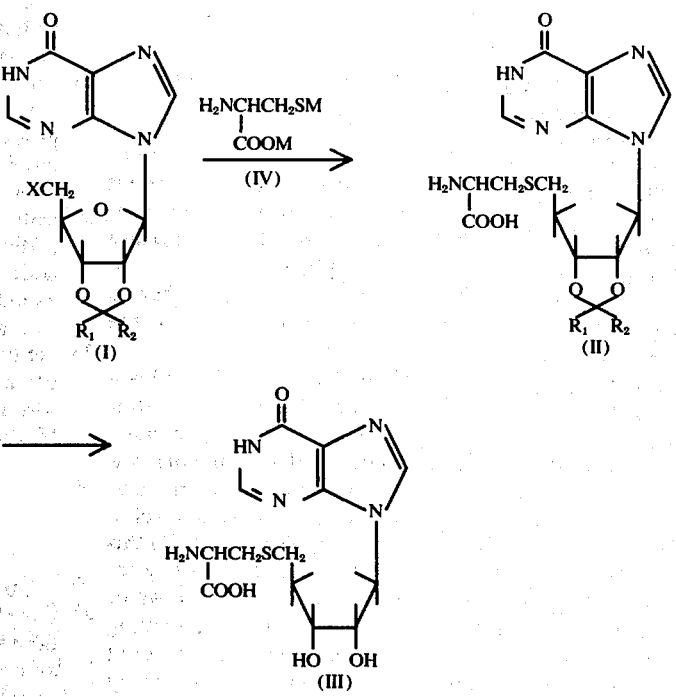

In the above formula $R_1$ and $R_2$ represent a hydrogen atom, a lower alkyl or aryl group, except that both $R_1$ and $R_2$ cannot be hydrogen atoms, M represents an alkali metal and X represents a halogen atom or the group Y-O wherein Y represents an arylsulfonyl or a lower alkylsulfonyl group.

The 2' and 3' hydroxy groups of the compound formula (I) can be protected by groups such as isopropylidene group in the case where both $R_1$ and $R_2$ are methyl groups, and other alkylidene, or arylidene groups which can be easily removed under mild conditions.

In the case where X of the compound of formula (I) is the Y-O group, the compound of formula (I) is reacted with the cysteine salt in liquid ammonia or, alternatively, in an alcohol solvent in the presence of an alkali metal alcoholate to produce the compound of formula (II). Examples of such alcohol solvents are methanol, ethanol, isopropanol and t-butanol. The salts of cysteine can be produced by reacting cystine or S-benzyl-cysteine with alkali metals in liquid ammonia.

In the case where X of a compound of the formula (I) represents a halogen atom, the compound of formula (I) is reacted with cysteine in an alcohol solvent in the presence of an alkali metal alcoholate to produce the compound of formula (II).

The reaction in alcohol solvents is conducted preferably from room temperature to reflux temperature, and the reaction in liquid ammonia is usually conducted under cold conditions, preferably at a temperature of $-80°$ to $-30°$ C.

Removal of the protecting groups of the compound of the formula (II) thus obtained may be easily effected by any known procedure such, for example, as by hydrolyzing them with organic acids such as dilute formic acid or mineral acids such as dilute hydrochloric acid or dilute sulfuric acid.

The following specific examples set forth procedures which can be used in producing the compound of the present invention.

EXAMPLE 1

S-(2',3'-O-isopropylideneinosyl)-L-cysteine:

Method A;

A flask with a mechanical stirrer and a soda lime or sodium hydroxide drying tube was charged with about 1 liter of liquid ammonia under cooling in a dry ice-acetone bath and with 6.6g of L-cystine. To this mixture thus obtained was added metallic sodium in such amount that the solution became pale blue. Then, a small amount of L-cystine was added to decolor the mixture.

To this solution was added 21.1g. of 2',3'-O-isopropylidene-5'-O-(p-toluenesulfonyl)inosine. After stirring for 4 hours, the mixture was allowed to stand overnight at room temperature so that ammonia was evaporated. The thus obtained residue was poured into ice water and the resulting mixture was weakly acidified by adding concentrated hydrochloric acid. To this was added ethanol to separate crystals, which were collected by filtration. Recrystallization from water afforded 16.6g of the desired product having a melting point of 195° to 198° C (decomposition). This product was further recrystallized to give white crystals having a melting point of 205° to 208° C (decomposition).

Elemental Analysis: as $C_{16}H_{21}N_5O_6S \cdot H_2O$
Calculated (%): C, 44.75 : H, 5.40 : N, 16.31.
Found (%): C, 44.61 : H, 5,32 : N, 15,97.

Method B 176 mg. of L-cysteine hydrochloride and 100 mg. of metallic sodium were dissolved in 20 ml of ethanol and to the resulting solution was added 463 mg of 2',3'-O-isopropylidene-5'-O-(p-toluenesulfonyl) inosine. The thus obtained mixture was refluxed for 5 hours. After cooling, crystals were collected by filtration, and were dissolved in 3 ml of acetic acid. To this solution was added ethanol to separate crystals, which were collected by filtration. The product was chromatographed over a silica gel and there was obtained 82 mg. of the desired product having a melting point of 193° to 197° C (decomposition). The paper chromatography of the product was identical with that of the sample obtained by Method A.

Method C 180 mg of L-cysteine hydrochloride and 100 mg of metallic sodium were dissolved in 20 ml of ethanol and to the resulting solution was added 270 mg of 5'-chloro-5'-deoxy-2',3'-O-isopropylideneinosine. The thus obtained mixture was refluxed for 5 hours. After cooling, to the reaction mixture was added 3 ml of acetic acid and the solvent was evaporated under reduced pressure to give a residue. To this was added hot ethanol and precipitates were collected by filtration. This substance was chromatographed over a silica gel and there was obtained 250 mg of the desired product having a melting point of 195 to 199° C (decomposition). The paper chromatography of this compound was identical with that of the sample obtained by Method A.

Method D

In a container as described in Method A was placed about 200 ml of liquid ammonia and to this was added 210 mg of L-cystine. To the mixture thus obtained was added metallic sodium in such amount that the solution become pale blue. Then, a small amount of L-cystine was added to decolor the mixture.

To this solution was added 560 mg of 2',3'-O-isopropylidene-5-O-methanesulfonylinosine. Liquid ammonia was evaporated with stirring over a period of 6 hours. The thus obtained residue was poured into ice water and the resulting solution was weakly acidified by adding concentrated hydrochloric acid. To this was added ethanol to separate crystals, which were collected by filtration. This product was chromatographed over a silica gel resulting in 150 mg of the desired product having a melting point of 198 to 203° C (decomposition). The paper chromatography of this compound was identical with that of the sample obtained by Method A.

EXAMPLE 2

S-inosyl-L-cysteine

Method A:

2.0 g. of S-(2,40,3'-O-isopropylideneinosyl)-L-cysteine obtained in Example 1 was dissolved in 10 ml of 60% formic acid solution. The resulting solution was allowed to stand at room temperature for 6 days. Then, to this was added ethanol to separate crystals, which were collected by filtration. This product was chromatographed over a silica gel and there was obtained 1.4 g of crystals having a melting point of 227° to 230° C (decomposition).

Elemental Analysis: as $C_{13}H_{17}N_5O_6S$
Calculated (%): C. 42.04: H, 4.62: N, 18.86.
Found (%): C. 42.35; H, 4.95: N, 18.41.

Method B

In a container as described in Method A was placed about 200 ml. of liquid ammonia and to the resulting solution was added 1.0 g of L-cystine. To the mixture thus obtained was added metallic sodium in such amount that the solution became pale blue. Then, a small amount of L-cystine was added to decolor the mixture.

To this solution was added 3.4 g of 2',3'-O- benzylidene-5'-O-methanesulfonylinosine. Liquid ammonia was evaporated with stirring over a period of 6 hours. The thus obtained residue was poured into ice water and the resulting solution was weakly acidified by adding concentrated hydrochloric acid. To this was added ethanol to separate crystals, which were collected by filtration. This product was recrystallized from methanol water, and there was obtained 0.8 g. of S-(2',3'-O-benzylideneinosyl)-L-cysteine having a melting point of 176° to 179° C. This was dissolved in 5 ml of 30% acetic acid solution and the resulting solution was reacted at 70° C for 6 hours. After the completion of the reaction, the solution was evaporated under reduced pressure to dryness to obtain the residue, which was chromatographed over a silica gel and there was obtained 0.5 g of crystals having a melting point of 221° to 225° C (decomposition). The paper chromatography of the product was identical with that of the sample obtained by Method A in Example 2.

The S-inosylsteine of the present invention posses excellent cell-proliferating and anti-ulcer activities. These effects are illustrated in the following examples and compared with properties of known related compounds.

(A) Cell-Proliferating Activity

A. Effect of S-inosylcysteine on proliferation of chick embryo heart cells.

Experiment 1

Method: The hearts excised from 13-day-old chick embryos were cut into pieces 1 to 2 mm in diameter under sterile conditions. After washing with calcium and magnesium-free phosphate buffered saline (PBS), the pieces of hearts were treated with a solution of 0.1% trypsin in PBS freed from calcium and magnesium ions, and the supernatant fraction was discarded. The residue was treated with a solution of 0.1% trypsin in PBS freed from calcium and magnesium ions, and the supernatant fractions containing isolated cells were collected. The procedure was repeated 3 times. The supernatant fractions were combined and diluted with cold culture medium containing 10% fetal calf serum, sodium penicillin G (100 units per ml) and sulfate streptomycin (1 μg per ml), and centrifuged at 150xG. The resulting pellet was washed twice with the culture medium and diluted cautiously with the same culture medium to give a suspension which contains 200,000 cells per ml. One ml of the suspension was poured into each of 28 culture tubes which were equally divided into 7 groups. The cells were cultured at 37° C in an incubator. After 1 day of incubation the culture medium of the tubes was removed and 1 ml of each culture medium containing compound shown in Table I was added thereto. After additional 3 days of incubation the culture medium was removed and the cells were then treated with 1 ml of 0.1 M citric acid containing 0.1% crystal violet. The number of cells was counted with a hemocytometer in quadruplicate after vigorous shaking. The results are shown in Table I.

Table 1.

| Tested compound (50 μg/ml) | | Cell number + S.E. (×10⁴ cells) | Growth rate % |
|---|---|---|---|
| | control | 50.9 ± 4.1 | 100.0 |
| (1) | S-inosyl-L-cysteine | 65.4 ± 1.6 | 128.5 |
| (2) | inosine | 54.1 ± 2.0 | 106.3 |
| (3) | adenosine | 44.1 ± 5.6 | 86.6 |
| (4) | L-cysteine | 50.5 ± 1.3 | 99.2 |
| (5) | inosine + L-cysteine | 57.8 ± 1.8 | 113.6 |
| (6) | adenosine + L-cysteine | 49.8 ± 0.2 | 97.8 |

Experiment 2

Method: The culture procedure for chick embryo heart cells was employed as described in Experiment 1. After 3 days of incubation, the culture medium was removed and 1 ml of each culture medium containing compounds shown in Table II was added thereto. After an additional 1 day of incubation the number of cells was counted. Result: The results are shown in Table II.

Table II

| Tested compound (20 μg/ml) | | Cell number ± S.E. (×10⁴ cells) | Growth rate (%) |
|---|---|---|---|
| | control | 81.6 ± 2.0 | 100.0 |
| (1) | S-inosyl-L-cysteine | 97.8 ± 3.8 | 119.9 |
| (7) | S-inosyl-L-homocysteine | 78.2 ± 7.5 | 95.8 |
| (8) | S-adenosyl-L-cysteine | 74.8 ± 4.7 | 91.7 |
| (9) | S-adenosyl-L-homocysteine | 71.5 ± 3.4 | 87.6 |
| (10) | S-guanosyl-L-homocystein | 69.2 ± 1.8 | 84.8 |

(b) Effect of S-inosyl cysteine on proliferation of check embryoheart cells in the presence of a growth inhibitor.

Experiment 3

Method: The culture procedure for chick embryo heart cells was employed as described in Experiment 1. After one day of incubation, the culture medium was removed and 1 ml of each culture medium containing KCN (1.7 μg per ml) and compounds shown in Table III were added thereto. The results are shown in Table III Table III

| Tested compound (50 μg/ml) | | Cell number ± S.E. (×10⁴ cells) | Growth Rate % | Growth rate (%) with respect to control of Table I.* |
|---|---|---|---|---|
| | control | 32.0 ± 5.0 | 100.0 | 62.9 |
| (1) | S-inosyl-L-cysteine | 50.9 ± 1.5 | 159.1 | 100.0 |
| (2) | inosine | 37.2 ± 4.4 | 116.3 | 73.1 |
| (3) | adenosine | 33.3 ± 1.9 | 104.1 | 65.4 |

Table III-continued

| Tested compound (50 μg/ml) | | Cell number ± S.E. (×10⁴ cells) | Growth Rate % | Growth rate (%) with respect to control of Table I.* |
|---|---|---|---|---|
| (4) | L-cystein | 41.9 ± 6.3 | 130.9 | 82.3 |
| (5) | inosine + L-cysteine | 42.3 ± 3.7 | 132.2 | 83.1 |
| (6) | adenosine + L-cysteine | 36.0 ± 4.0 | 112.5 | 70.7 |

*This experiment and Experiment 1 were simultaneously carried out.

Table IV.

Experiment 4
Method; Same as in Experiment 2 except that KCN (1.7 μg per ml) was added to each culture medium.
The results are shown in Table IV

| Tested Compound (20 μg/ml) | | Cell number ± S.E. (×10⁴cells | Growth rate (%) | Growth rate (%) with respect to control of Table II* |
|---|---|---|---|---|
| | CONTROL | 65.8 ± 0.8 | 100.0 | 80.6 |
| (1) | S-inosyl-L-cysteine | 85.6 ± 0.4 | 130.1 | 104.9 |
| (7) | S-inosyl-L-homocysteine | 73.5 ± 1.7 | 111.7 | 90.1 |
| (8) | S-adenosyl-L-cysteine | 64.2 ± 3.0 | 97.6 | 78.7 |
| (9) | S-adensyl-L-homocysteine | 65.2 ± 1.8 | 99.1 | 79.9 |
| (10) | S-guanosyl-L-homocysteine | 66.3 ± 1.4 | 100.8 | 81.3 |

*This experiment and Experiment 2 were simultaneously carried out.

Table V

Experiment 5
Method: Same as in Experiment 2 except that 6-mercaptopurine (5 μg per ml) was added to each culture medium.
The results are shown in Table V.

| Tested compound (20 μg/ml) | | Cell number ± S.E. (×10⁴cells) | Growth Rate (%) | Growth rate (%) with respect to control of Table II.* |
|---|---|---|---|---|
| | control | 68.3 ± 0.4 | 100.0 | 83.7 |
| (1) | S-inosyl-L-cysteine | 85.8 ± 2.9 | 125.6 | 105.1 |
| (7) | S-inosyl-L-homocysteine | 65.3 ± 3.7 | 95.6 | 80.0 |
| (8) | S-adenosyl-L-cysteine | 70.7 ± 1.2 | 103.5 | 86.6 |
| (9) | S-adenosyl-L-homocysteine | 75.7 ± 1.6 | 110.8 | 92.8 |
| (10) | S-guanosyl-L-homocysteine | 72.3 ± 5.5 | 105.9 | 88.6 |

*This experiment and Experiment 2 were simultaneously carried out.

As can be seen in Tables I to V, the ability to accelerate cellproliferation caused by S-inosycysteine of the present invention is superior to those of known related compounds (2) to (10).

B. Anti-Ulcer Activity
a. Effect of S-inosylcysteine on pylorus ligation ulcer.

Experiment 6

Method: Male Wister rats (Keari Gifu-Lab.), aged 7 weeks were used. After fasting for 48 hours, rats weighing 210 to 230 g were divided into 6 groups of 10 rats. The pylorus of stomach was ligated under light anesthesia with pentobarbital sodium (25 mg per kg, i.p.). Immediately after the ligation, a psysiological saline was orally administered to one group and a solution of each tested compound (50 mg per kg) was orally administered to the remaining 5 groups. After these rats were kept without food and water for 10 hours from the ligation, the stomach was removed under anesthesia with pentobarbital sodium (30 mg per kg, i.p.). The gastric contents were aspirated and the stomach was fixed by means of the injection of 10 ml of a 2% formalin solution into the lumen. The stomach was opened along its greater curvature. The severity of the lesion of the rumen, that is, the degree of ulcer was expressed as ulcer index according to the method of Yokotani (Folia pharmacol. Japon. 56, 1373, (1960). The results are shown in Table VI.

Table VI

| | Tested compound (50 mg/kg, p.o.) | Mean ulcer index ± S.E. | Inhibition rate (%)* |
|---|---|---|---|
| | control (physiological saline) | 13.9 ± 0.5 | — |
| (1) | S-inosyl-L-cysteine | 8.1 ± 1.1 | 42 |
| (7) | S-inosyl-L-homocysteine | 12.3 ± 1.1 | 12 |
| (8) | S-adenosyl-L-cysteine | 12.1 ± 1.2 | 13 |
| (9) | S-adenosyl-L-homocystein | 11.3 ± 0.7 | 19 |

Table VI-continued

| | Tested compound (50 mg/kg, p.o.) | Mean ulcer index ± S.E. | Inhibition rate (%)* |
|---|---|---|---|
| (10) | S-guanosyl-L-homocysteine | 15.0 ± 1.8 | −8 |

*Inhibition rate was calculated as follows:

$$\text{Inhibition rate (\%)} = \frac{\text{Ulcer index (control)} - \text{Ulcer index (tested compound)}}{\text{Ulcer index (control)}} \times \phi$$

Table VII

Experiment 7
Method: The same method as described in Experiment 6 was employed. The effect of S-inosyl-L-cysteine on pylorus ligation ulcer was examined with intramuscular administration. The results are shown in Table Vii.

| Tested compound (50 mg/kg, i.m.) | Mean ulcer index ± S.E. | Inhibition rate (%) |
|---|---|---|
| control (physiological saline) | 12.5 ± 2.6 | — |
| (1) S-inosyl-L-cysteine | 5.1 ± 1.6 | 59 | b. Effect of S-inosylcysteine on gastric secretion.
Method: The rats were ligated in the same manner as in Experiment 6, and divided into 2 groups of 10 rats.

Immediately after the ligation, a physiological saline or a solution of S-inosyl-L-cysteine was orally administered. After the rats were kept without food and water for 5 hours from the ligation, the esophagus was ligated and the stomach was removed under anesthesia with pentobarbital sodium (30 mg per kg. i.p.). The gastric contents were collected and centrifuged at 2,000 rpm for 10 minutes. The volume of supernatant was measured and its pH was determined with a pH meter (Hitach-Horiba Type M-5). Free-HCl, total-HCl and total-acidity in the supernatant were determined by the titration with 1/50 N NaOH using Topfer's solution and phenolphtalein solution as an indicator.

Table VIII

| Test compound (50 mg/kg, p.o.) | Volume (ml ± S.E.) | Inhibition rate (%) | pH | Free-HCl mEq/l ± S.E. | Free-HCl Inhibition rate % | Total-HCl mEq/l ± S.E. | Total-HCl Inhibition rate (%) | Total-acidity mEq/l ± S.E. | Total-acidity Inhibition rate (%) |
|---|---|---|---|---|---|---|---|---|---|
| Control | 8.6 ± 0.5 | — | 1.38 ± 0.03 | 67.0 ± 4.2 | — | 95.8 ± 4.2 | — | 106.0 ± 3.6 | — |
| (1) S-inosyl-L-cysteine | 5.3 ± 0.5 | 38 | 1.50 ± 0.06 | 42.8 ± 6.0 | 36 | 73.8 ± 6.4 | 23 | 83.2 ± 6.2 | 22 |

As can be seen in Tables VI to VIII, the anti-ulcer properties of the S-inosyl cysteine of the present invention is superior to those of known related compounds (7) to (10).

It should be evident that various modifications can be made to the described embodiments without departing from the scope of the present invention.

We claim as our invention:
1. S-inosylcysteine.

* * * * *